United States Patent
Tischendorf

(10) Patent No.: US 11,794,018 B2
(45) Date of Patent: Oct. 24, 2023

(54) IMPLANTABLE MEDICAL DEVICE FOR TREATING ARRHYTHMIAS

(71) Applicant: Medtronic, Inc., Minneapolis, MN (US)

(72) Inventor: Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 457 days.

(21) Appl. No.: 17/150,250

(22) Filed: Jan. 15, 2021

(65) Prior Publication Data

US 2022/0226652 A1    Jul. 21, 2022

(51) Int. Cl.

| A61N 1/362 | (2006.01) |
| A61B 5/363 | (2021.01) |
| A61N 1/05 | (2006.01) |
| A61K 31/7076 | (2006.01) |
| A61M 5/168 | (2006.01) |

(52) U.S. Cl.
CPC ............ *A61N 1/3629* (2017.08); *A61B 5/363* (2021.01); *A61K 31/7076* (2013.01); *A61M 5/16813* (2013.01); *A61N 1/0568* (2013.01); *A61M 2205/04* (2013.01); *A61M 2205/054* (2013.01); *A61M 2205/3523* (2013.01); *A61M 2205/50* (2013.01); *A61M 2210/125* (2013.01); *A61M 2230/06* (2013.01)

(58) Field of Classification Search
CPC .... A61N 1/3629; A61N 1/0568; A61B 5/363; A61K 31/7076; A61M 5/16813; A61M 2205/04; A61M 2210/125
See application file for complete search history.

(56) References Cited

U.S. PATENT DOCUMENTS

| 4,485,813 A | 12/1984 | Anderson et al. |
| 5,052,388 A | 10/1991 | Sivula et al. |
| 5,507,782 A | 4/1996 | Kieval et al. |
| 5,593,431 A | 1/1997 | Sheldon |
| 5,885,471 A | 3/1999 | Ruben et al. |
| 6,044,297 A | 3/2000 | Sheldon et al. |
| 7,547,301 B2 | 6/2009 | Altman et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 9,775,982 B2 | 10/2017 | Grubac et al. |
| 2008/0195160 A1* | 8/2008 | Wingeier ............. A61N 1/0529 607/2 |
| 2012/0265087 A1* | 10/2012 | Lian .................... A61B 5/4839 600/515 |
| 2018/0161580 A1* | 6/2018 | Demmer ............. A61N 1/3688 |

* cited by examiner

*Primary Examiner* — Bradley J Osinski
(74) *Attorney, Agent, or Firm* — Shumaker & Sieffert, P.A.

(57) ABSTRACT

Techniques are disclosed for treating arrhythmias using an implantable medical device. An implantable medical device that is adapted for implantation wholly within a heart chamber of the heart of a patient may include a reservoir containing one or more therapeutically useful doses of a drug for treating an arrhythmia. The implantable medical device may include processing circuitry configured to detect an occurrence of the arrhythmia in the heart of the patient. The implantable medical device may include a valve operable to be opened in response to detecting the occurrence of the arrhythmia in the heart of the patient to release a therapeutically useful dose of the drug into the heart of the patient to treat arrhythmia of the heart.

20 Claims, 4 Drawing Sheets

IMPLANTABLE MEDICAL DEVICE FOR TREATING ARRHYTHMIAS

TECHNICAL FIELD

This disclosure generally relates to medical devices and, more particularly, an implantable medical device.

BACKGROUND

Implantable cardiac pacemakers are often placed in a subcutaneous pocket and coupled to one or more transvenous medical electrical leads carrying pacing and sensing electrodes positioned in the heart. Intracardiac pacemakers have recently been introduced that are implantable within a ventricular chamber of a patient's heart for delivering ventricular pacing pulses without the use of electrical leads. Such pacemakers or other implantable medical devices may also be able to detect the occurrence of arrhythmias, such as fibrillation, tachycardia and bradycardia, in the patient's heart.

A high-voltage implantable cardiac defibrillator may deliver electrical shocks to the patient's heart in response to detection of a tachycardia or fibrillation to restore a normal heartbeat in the patient. In some cases, a single implantable medical device functions as both an implantable pacemaker and implantable cardiac defibrillator. In some cases, a system of two or more devices having respective pacing and defibrillation functionality may be implanted in the patient and outside of the aforementioned leadless pacemaker, generally have electrical leads connecting the device to the heart to deliver therapy.

SUMMARY

In general, the disclosure describes techniques for treating arrhythmias sensed by an implantable medical device (IMD) that is implanted in a patient's heart. The IMD may carry one or more doses of drugs for treating arrhythmias, such as adenosine for the treatment of tachycardias. The IMD may detect the occurrence of an arrhythmia and, in response to determining the occurrence of the arrhythmia, release one or more doses of the drugs carried by the IMD into the walls of the patient's heart or the patient's bloodstream, thereby treating the arrhythmia of the patient's heart to restore a normal heartbeat in the patient. The IMD may, in one example, sense, via one or more electrodes, electrogram data of the heart of the patient and may analyze the electrogram data to determine the occurrence of an arrhythmia. In other examples, the IMD may use any other suitable techniques to determine the occurrence of an arrhythmia, such as by using an accelerometer or by receiving communication from another device, such as a cardiac monitor, that is operable to detect the occurrence of an arrhythmia.

The techniques of the disclosure provide specific improvements to the technical field of implantable medical devices that have practical applications. For example, the use of the techniques herein may enable an implantable medical device such as an intracardiac pacemaker to sense and treat detected arrhythmias with or without the use of a separate implantable cardiac defibrillator that is implanted in the patient.

In one example, this disclosure describes an implantable medical device comprising: processing circuitry configured to detect an occurrence of an arrhythmia in a heart of a patient; a reservoir containing one or more therapeutically useful doses of a drug for treating the arrhythmia; and a valve operable to be opened in response to detecting the occurrence of the arrhythmia in the heart of the patient to release a therapeutically useful dose of the drug into the heart of the patient to treat arrhythmia of the heart; wherein the implantable medical device is adapted for implantation wholly within a heart chamber of the heart of the patient.

In another example, this disclosure describes a method comprising: detecting, by processing circuitry of an implantable medical device, an occurrence of an arrhythmia in a heart of a patient; and in response to detecting the occurrence of the arrhythmia, releasing, by the implantable medical device, a therapeutically useful dose of a drug for treating the arrhythmia from a reservoir in the implantable medical device that contains one or more therapeutically useful doses of the drug for treating the arrhythmia into the heart of the patient; wherein the implantable medical device is adapted for implantation wholly within a heart chamber of the heart of the patient.

In another example, this disclosure describes an implantable medical device comprising: one or more electrodes configured to sense electrogram data from a heart of a patient; a reservoir containing one or more therapeutically useful doses of a drug for treating an arrhythmia; a port for releasing the drug into the heart of the patient, wherein the port is disposed at a distal end of the implantable medical device; a valve operable to be opened and closed; and processing circuitry configured to: detect, based on the electrogram data, an occurrence of the arrhythmia in the heart of the patient; and in response to detecting the occurrence of the arrhythmia in the heart of the patient, cause the valve to be opened to release a therapeutically useful dose of the drug out of the port into the heart of the patient to treat arrhythmia of the heart; wherein the implantable medical device is adapted for implantation wholly within a heart chamber of the heart of the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

In general, this disclosure describes techniques for an IMD that may contain one or more doses of a drug for treating an arrhythmia and may, in response to detecting the occurrence of the arrhythmia in the heart, release one or more doses of the drug contained in the IMD into the heart walls and/or bloodstream of the heart to treat the arrhythmia. The techniques disclosed herein enable an IMD that is implanted wholly within a heart chamber to not only be able to detect the occurrence of arrhythmias, but to also treat the detected arrhythmias without the use of a separate implantable cardiac defibrillator that is implanted in the patient.

Due to the relatively small size of an IMD that is adapted for implantation wholly within a heart chamber of the heart of a patient, the IMD may, in some examples, contain no more than two or three therapeutically useful doses of a drug for treating arrhythmia. The IMD described in this disclosure may therefore be used in situations where there is not yet a medical justification to implant a high-voltage implantable cardiac defibrillator in the patient for treating the occurrences of arrhythmias in the patient, or may be used in conjunction with a high-voltage implantable cardiac defibrillator as a backup device for treating arrhythmia. When the IMD detects the occurrence of an arrhythmia and, in response, releases a dose of the drug to treat the arrhythmia, the IMD may communicate to an external device an indication that the IMD has detected a treatable arrhythmia and/or released a dose of the drug, and such information communicated by the IMD may be used by clinicians or other medical professions to determine whether there is a medical justification to implant a high-voltage implantable cardiac defibrillator in the patient.

Figure 1:
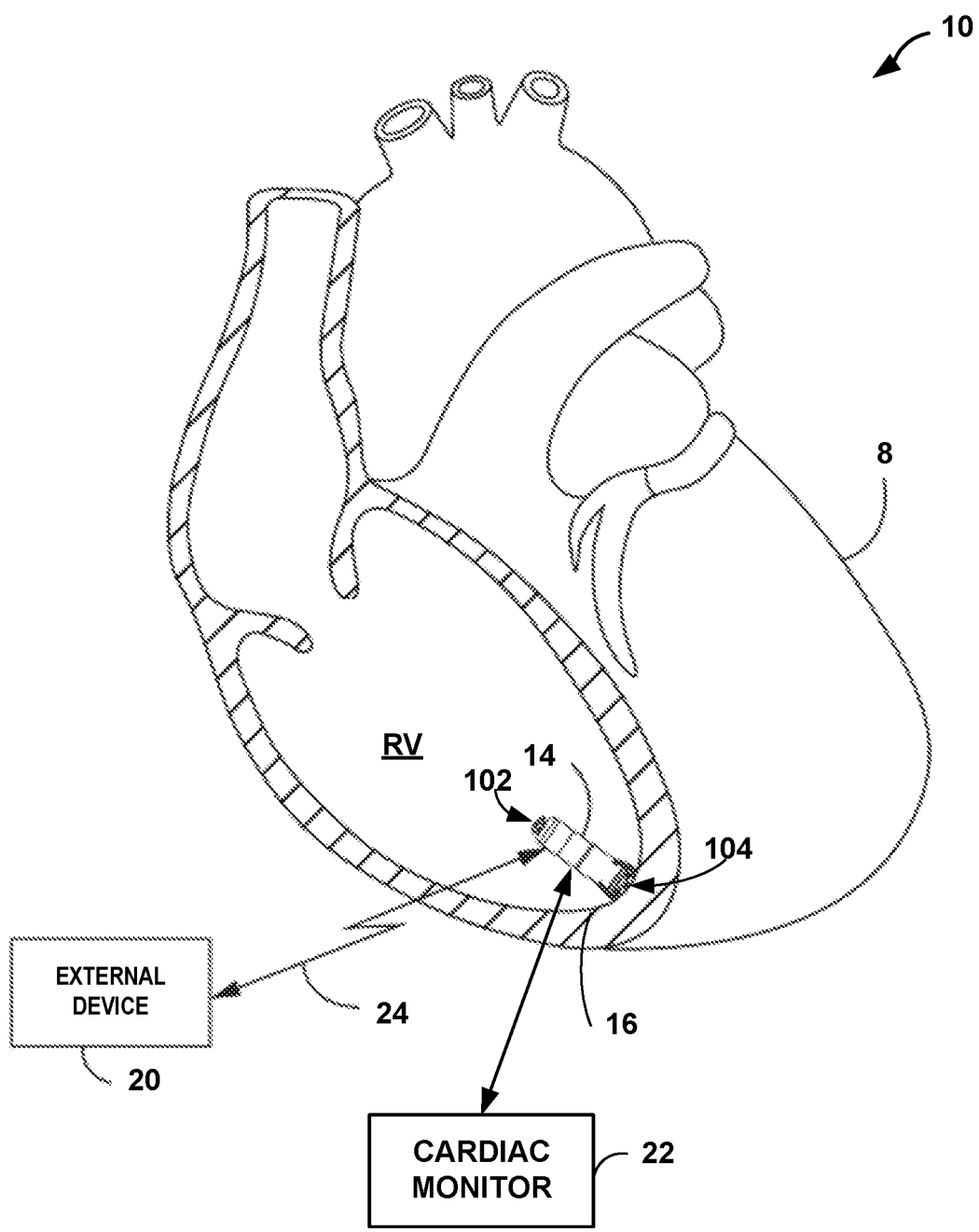
FIG. 1 is a conceptual diagram illustrating a medical device system including an implantable medical device (IMD) that may be used to detect the occurrence of an arrhythmia in a heart of a patient and to release a therapeutically useful dose of a drug to treat the detected arrhythmia, in accordance with the techniques of the disclosure.

FIG. 1 is a conceptual diagram illustrating a medical device system 2 including an implantable medical device (IMD) 14 that may be used to detect the occurrence of an arrhythmia in a heart 8 of a patient and to release a therapeutically useful dose of a drug to treat the detected arrhythmia, in accordance with the techniques of the disclosure. As shown in FIG. 1, medical device system 10 includes IMD 14 and external device 20.

IMD 14 is an intracardiac medical device adapted for implantation in the patient, such as for implantation wholly within a heart chamber, such as wholly within the right ventricle (RV), right atrium (RA), left atrium (LA), or left ventricle (LV) of heart 8, for sensing cardiac signals to detect the occurrence of arrhythmias and to release one or more doses of drugs into heart 8 to treat the detected arrhythmias. In some examples, IMD 14 may be an intracardiac pacemaker adapted for implantation wholly within a heart chamber of heart 8 that, in addition to sensing cardiac signals, detecting arrhythmias, and releasing drugs to treat detect arrhythmias, delivers pacing pulses. In some examples, IMD 14 may be operably coupled to a sensing electrode that is located in another heart chamber different from the heart chamber in which IMD 14 is implanted.

IMD 14 is reduced in size compared to subcutaneously implanted pacemakers and may be generally cylindrical in shape to enable transvenous implantation via a delivery catheter. However, in other examples of the techniques of the disclosure, medical device system 10 may include other types of IMDs in addition to or in the alternative to an intracardiac medical device not expressly described herein.

As depicted in the example of FIG. 1, IMD 14 may positioned along a heart wall 16 (e.g., an endocardial wall) of the RV, e.g., near the RV apex. Specifically, IMD 14 may include proximal end 102 and distal end 104. Distal end 104 is referred to as "distal" in that it is expected to be placed against a targeted site in heart 7, such as contacting the heart wall 16 of heart 8. As shown in FIG. 1, IMD 14 may be positioned in the RV of heart 8 such that distal end 102 of IMD 14 may be place against heart wall 16 of heart 8 and may be nearer to heart wall 16 compared with proximal end 102 of IMD 14.

The techniques disclosed herein are not limited to the location of IMD 14 shown in the example of FIG. 1 and IMD 14 may be implanted at other positions within heart 8. For example, an intracardiac pacemaker may be positioned at different locations in the RV, such as along the interventricular septum, in the LV, in the RA, or epicardially. Further, the techniques disclosed herein are not limited to an IMD that is implanted within heart 8 and are not limited to detecting and treating arrhythmias. For example, IMD 14 may be implanted in the clavicle region of patient, in the abdominal wall region of the patient, or in other regions of the patient other than heart 8.

In examples where IMD 14 is an intracardiac pacemaker, IMD 14 is capable of producing electrical stimulation pulses, e.g., pacing pulses, delivered to heart 8 via one or more electrodes on the outer housing of IMD 14. IMD 14 may be configured to deliver pacing pulses and sense cardiac electrogram signals via the same housing based electrodes.

IMD 14 may be configured to detect, based on signals sensed via one or more electrodes on the outer housing of IMD 14, the occurrence of an arrhythmia in heart 8 of the patient. For example, IMD 14 may be configured to detect the occurrence of a tachycardia in heart 8 or a bradycardia in heart 8. IMD 14 may, in response to detecting the occurrence of the arrhythmia in heart 8, release a therapeutically useful dose of a drug for treating the arrhythmia from a reservoir in IMD 14 that contains one or more therapeutically useful doses of the drug for treating the arrhythmia into heart 8. For example, if IMD 14 contains one or more doses of a drug, such as adenosine, for treating tachycardia in heart 8, IMD 14 may, in response to detecting the occurrence of tachycardia in heart 8, release a therapeutically useful dose of the drug for treating tachycardia into heart wall 16 of heart 8 and/or the bloodstream of heart 8. Similarly, if IMD 14 contains one or more doses of a drug for treating bradycardia in heart 8, IMD 14 may, in response to detecting the occurrence of bradycardia in heart 8, release a therapeutically useful dose of the drug for treating bradycardia into heart wall 16 of heart 8 and/or the bloodstream of heart 8.

IMD 14 may also be configured to detect, based on signals sensed via one or more electrodes on the outer housing of IMD 14, the occurrence of stable ventricular tachycardia or ventricular tachycardia in heart 8 of the patient. IMD 14 may, in response to detecting the occurrence of stable ventricular tachycardia or ventricular tachycardia in heart 8, release a therapeutically useful dose of a drug for treating the stable ventricular tachycardia or ventricular tachycardia from a reservoir in IMD 14. In some examples, if IMD 14 contains one or more doses of a drug, such as procainamide, for treating stable ventricular tachycardia in heart 8, IMD 14 may, in response to detecting the occurrence of a stable ventricular tachycardia in heart 8, release a therapeutically useful dose of the drug for treating tachycardia into heart wall 16 of heart 8 and/or the bloodstream of heart 8. In some examples, if IMD 14 contains one or more doses of a drug, such as lidocaine or bretylium, for treating ventricular tachycardia in heart 8, IMD 14 may, in response to detecting the occurrence of a ventricular tachycardia in heart 8, release a therapeutically useful dose of the drug for treating and preventing ventricular tachycardia into heart wall 16 of heart 8 and/or the bloodstream of heart 8.

In some examples, besides detecting the occurrence of arrhythmias in heart 8 of the patient, IMD 14 may also be configured to detect other conditions of the patient. For example, IMD 14 may be configured to detect the occurrence of atrial flutter. For example, IMD 14 may, in response to detecting the occurrence of atrial flutter in heart 8, release a therapeutically useful dose of a drug for treating the atrial flutter from a reservoir in IMD 14. For example, if IMD 14 contains one or more doses of a drug, such as ibutilide or dofetilide, for treating atrial flutter in heart 8, IMD 14 may, in response to detecting the occurrence of atrial flutter in heart 8, release a therapeutically useful dose of the drug for treating atrial flutter into heart wall 16 of heart 8 and/or the bloodstream of heart 8.

In some examples, IMD 14 may also be configured to detect, based on signals sensed via one or more electrodes on the outer housing of IMD 14, the occurrence of shock-refractory ventricular fibrillation in heart 8 of the patient. IMD 14 may, in response to detecting the occurrence of shock-refractory ventricular fibrillation in heart 8, release a therapeutically useful dose of a drug for treating the shock-refractory ventricular fibrillation from a reservoir in IMD 14. For example, if IMD 14 contains one or more doses of a drug, such as amiodarone, for treating shock-refractory ventricular fibrillation in heart 8, IMD 14 may, in response to detecting the occurrence of shock-refractory ventricular fibrillation in heart 8, release a therapeutically useful dose of the drug for treating shock-refractory ventricular fibrillation into heart wall 16 of heart 8 and/or the bloodstream of heart 8.

In some examples, IMD 14 may be configured to detect the occurrence of neurological conditions, such as epileptic seizures in the patient. For example, IMD 14 may, based on signals sensed via one or more electrodes on the outer housing of IMD 14, signals sensed via one or more electrodes placed on the brain of the patient, and the like, the occurrence of an epileptic seizure. IMD 14 may, in response to detecting the occurrence of the epileptic seizure, release a therapeutically useful dose of an anti-seizure drug, such as fosphenytoin, for treating the seizure to the brain of the patient.

In another example, IMD 14 may be configured to detect the occurrence of pain in the patient and, in response, release a therapeutically useful dose of pain medication or analgesic for treating the occurrence of pain in the patient. In some additional examples, IMD 14 may be configured to detect the occurrence of high blood sugar in the patient and, in response, release a therapeutically useful dose of drugs, such as insulin, for treating the occurrence of high blood sugar in the patient.

In some examples, IMD 14 may be configured to wirelessly communicate, such as using a radio frequency (RF) link such as BLUETOOTH®, Wi-Fi, Medical Implant Communication Service (MICS) or other communication bandwidth, with cardiac monitor 22 that is configured to detect the occurrence of arrhythmias in heart 8, such as tachycardias and/or bradycardias, in heart 8. In some examples, cardiac monitor 22 may be an IMD, such as in the form of a LINQ™ Insertable Cardiac Monitor (ICM), available from Medtronic plc, of Dublin, Ireland. In other examples, cardiac monitor 22 may be any other device configured to detect the occurrence of arrhythmias in hear 8, such as wearable devices (e.g., smart watches, Mobile Cardiac Telemetry devices, etc.) worn by the patient.

IMD 14 is capable of unidirectional or bidirectional wireless communication with external device 20, which may be a dedicated programmer for IMD 14 or other computing device configured to communicate with IMD 14. Aspects of external device 20 may generally correspond to the external programming/monitoring unit disclosed in U.S. Pat. No. 5,507,782 to Kieval, et al., entitled "Method and apparatus for dual chamber cardiac pacing," filed on Mar. 17, 1994 and issued on Apr. 16, 1996, the entire contents of which is incorporated herein by reference. External device 20 is typically used by a physician, technician, nurse, clinician or other qualified user for programming operating parameters in IMD 14. External device 20 may be located in a clinic, hospital or other medical facility. External device 20 may alternatively be embodied as a home monitor, a handheld device, or a smartphone that may be used in a medical facility, in the patient's home, or another location. Operating parameters, including sensing and therapy delivery control parameters, may be programmed into IMD 14 using external device 20.

External device 20 is configured for bidirectional communication with implantable telemetry circuitry included in IMD 14. External device 20 establishes a wireless communication link 24 with IMD 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate IMID 14 to establish and maintain a communication link 24, and in some other examples, external device 20 and IMD 14 may be configured to communicate using a distance telemetry algorithm and circuitry that does not require the use of a programming head and does not require user intervention to maintain a communication link.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a remote patient database may be configured to enable a clinician to review various data associated with IMD 14 and heart 8.

When IMD 14 releases a dose of a drug for treating an arrhythmia into heart 8, IMD 14 may, in response, communicate with external device 20 to send an indication of the drug release by IMD 14 to external device 20. External device 20 may receive the indication of the drug release from IMD 14 and may, for example, output an indication of the drug release from IMD 14, such as by displaying an indication of the drug release from IMD 14, thereby providing information to a clinician regarding medical treatment options regarding a patient, such as information regarding whether a high-voltage implantable cardiac defibrillator should be implanted in the patient.

Accordingly, the techniques set forth herein provide specific improvements to the technical field of implantable medical devices. For example, the use of the techniques herein may enable an IMD that is adapted for implantation wholly within a heart chamber of the heart of a patient to be able to detect the occurrence of an arrhythmia in the heart of the patient and to release a therapeutically useful dosage of drugs for treating arrhythmias into the heart wall or bloodstream of the heart of the patient. The ability of such an IMD implanted wholly within a heart chamber of a heart to detect and treat arrhythmias may obviate the use of a separate implantable cardiac defibrillator that is implanted in the patient, thereby potentially reducing the amount of surgery performed on a patient and potentially reducing the amount of medical devices implanted in the patient. Further, by outputting an indication of drug release to an external programmer each time the IMD releases a dose of a drug for treating an arrhythmia, the techniques described herein provides data that may better inform clinicians as to whether a cardiac defibrillator should be implanted in the patient, thereby enabling clinicians to make more informed decisions regarding medical treatments for the patient.

Figure 2A:
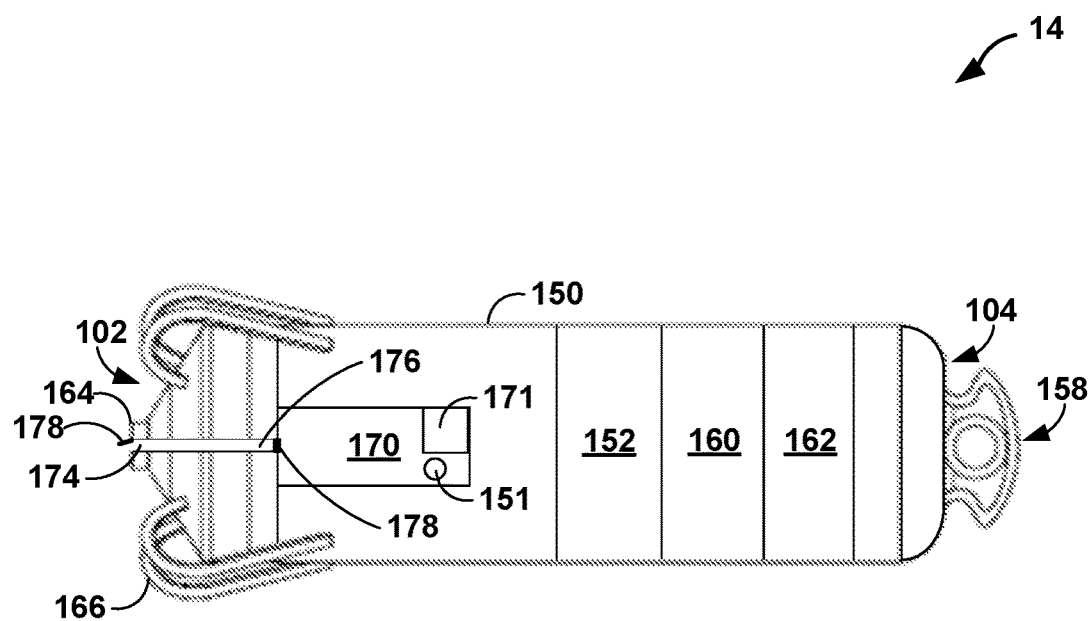
FIGS. 2A and 2B are conceptual diagrams illustrating examples of the IMD of FIG. 1 in accordance with the techniques of the disclosure.
Figure 2B:
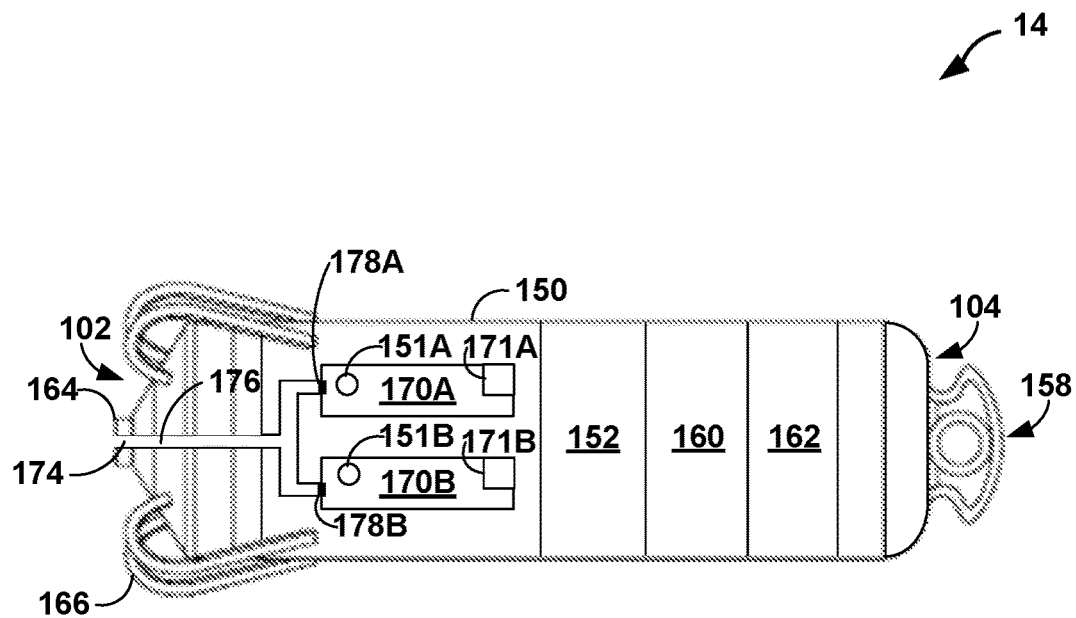

FIGS. 2A and 2B are conceptual diagrams illustrating examples of IMD 14 of FIG. 1 in accordance with the techniques of the disclosure. Because IMD 14 is adapted for implantation wholly within a heart chamber of the heart 8 of the patient, such as being adapted for implantation wholly within a right ventricle of the heart 8, IMD 14 may be relatively small. For example, IMD 14 may have a volume of less than one cubic centimeter (cc), a length of less than 30 millimeters (mm), and an outer diameter of less than 7 mm.

As shown in FIG. 2A, IMD 14 includes electrodes 162 and 164 spaced apart along the housing 150 of IMD 14 for sensing electrogram data from heart 8 of FIG. 1. In some examples, electrodes 162 and 164 may also deliver pacing pulses to heart 8. Electrode 164 is shown as a tip electrode extending from a distal end 102 of IMD 14, and electrode 162 is shown as a ring electrode along a mid-portion of housing 150, for example adjacent proximal end 104. Distal end 102 is referred to as "distal" in that it is expected to be the leading end as IMD 14 is advanced through a delivery tool, such as a catheter, and placed against a targeted pacing site, such as against heart wall 16 in the right ventricle of heart 8.

Electrodes 162 and 164 form an anode and cathode pair for bipolar cardiac pacing and sensing. In alternative embodiments, IMD 14 may include two or more ring electrodes, two or more tip electrodes, and/or other types of electrodes exposed along pacemaker housing 150 for delivering electrical stimulation to heart 8 and sensing electrogram data. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along IMD 14 other than the locations shown. In some examples, electrodes 162 and 164 may not be separate components to housing 150. For example, housing 150 may incorporate electrodes 162 and 164 or may otherwise be operable to act as electrodes 162 and 164 described herein.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generation circuit and electrogram sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 contains a control electronics subassembly 152, which houses the electronics for sensing cardiac signals, producing pacing pulses when IMD 14 performs pacing functionality, and controlling therapy delivery and other functions of IMD 14 as described in further detail below with respect to FIG. 3. Housing 150 further contains a battery subassembly 160, which provides power to the control electronics subassembly 152. Additional description of batteries implemented by battery subassembly 160 may be found in U.S. Pat. No. 8,433,409 to Johnson, et al., entitled "Implantable medical device battery," filed on Jan. 29, 2010, and issued on Apr. 30, 2013 and in U.S. Pat. No. 8,541,131 to Lund, et al., entitled "Elongate battery for implantable medical device," filed on Aug. 28, 2009, and issued on Sep. 24, 2013, the entire contents of each of which are incorporated herein by reference.

IMD 14 may include a set of fixation tines 166 at distal end 102 to secure IMD 14 to patient tissue, e.g., by actively engaging with the ventricular endocardium and/or interacting with the ventricular trabeculae. Fixation tines 166 are configured to anchor IMD 14 to position electrode 164 in operative proximity to a targeted tissue (e.g., heart wall 16) for delivering therapeutic electrical stimulation pulses. Numerous types of active and/or passive fixation members may be employed for anchoring or stabilizing IMD 14 in an implant position. Additional detail with respect to fixation tines 166 may be found in U.S. Pat. No. 9,775,982 to Grubac, et al., entitled "Implantable medical device fixation," filed on Apr. 28, 2011 and issued on Oct. 3, 2017, the entire content of which is incorporated herein by reference.

IMD 14 may optionally include a delivery tool interface 158. Delivery tool interface 158 may be located at the proximal end 104 of IMD 14 and is configured to connect to a delivery device, such as a catheter, used to position IMD 14 at an implant location during an implantation procedure, for example within a heart chamber.

In accordance with aspects of the present disclosure, IMD 14 may include reservoir 170 within housing 150 that contains one or more therapeutically-useful doses of drugs for treating arrhythmias. Reservoir 170 may be formed of any suitable material, such as steel, plastic, and the like, for containing drugs for treating arrhythmias. For example, reservoir 170 may contain adenosine for treating tachycardias. In some examples, reservoir 170 may include refill port 151 for refilling reservoir 170. Refill port 151 may extend from reservoir 170 through to an opening of housing 150, so that reservoir 170 may be refilled through refill port 151.

Due to the small size of IMD 14, reservoir 170 may correspondingly be relatively small. For example, the volume of reservoir 170 may be between 1 cc to 2 cc. A drug for treating arrhythmias, such as adenosine, may have a solubility in water of between 30 milligrams (mg) per milliliter (mL) to 50 mg/ML, and a single therapeutically useful dose of adenosine may range from 6 mg to 25 mg. Thus, reservoir 170 that contains 1 mL of adenosine may contain enough adenosine for delivering at least two therapeutically useful dosages of adenosine to heart 8.

In some examples, to make room within the interior of IMD 14 for reservoir 170 having a volume between 1 cc to 2 cc, the size of control electronics subassembly 152 and/or battery subassembly 160 may be reduced compared with similar IMDs (e.g., an intracardiac pacemaker) that do not contain a reservoir of drugs for treating arrhythmias. For example, the electronic circuitry in control electronics subassembly 152. For example, if IMD 14 does not perform pacemaker functionality, the size of the battery in battery subassembly 160 may be reduced compared with the battery in a similarly-sized intracardiac pacemaker while still providing, for example, five to ten years of battery life for IMD 14. In some examples, the size of the electronics in control electronics subassembly 152 may be reduced via use of three-dimensional stacked electronics or other suitable techniques to maximize the available space within IMD 14 for reservoir 170 and battery subassembly 160.

Housing 150 of IMD 14 may include port 174, which may be an opening in housing 150 of IMD 4 connected to reservoir 170 via tube 176 for outputting the drugs contained in reservoir 170 into a heart wall of heart 8 and/or the bloodstream of heart 8 when IMD 14 releases one or more doses of the drug from reservoir 170. In some examples, port 174 may be situated on distal end 102 of IMD 104. Because distal end 102 of IMD 14 may be situated against heart wall 16 of, e.g., the right ventricle of heart 8, releasing the drugs out of port 174 at distal end of 102 of IMD 14 may enable the drugs to be released into the heart walls of heart 8. In some examples, IMD 14 includes tube 176, which may be any hollow structure coupled between reservoir 170 and port 174 for conveying drugs from reservoir 170 to port 174, so that the drugs contained within reservoir 170 may flow out of reservoir 170 to port 174 to release the drugs into the heart wall of heart 8 and/or the bloodstream of heart 8.

In some examples, as shown in FIG. 2A, tube 176 may extend through or near electrode 164. In some examples, tube 176 may be conductive. In some examples, control electronics subassembly 152 may be electrically connected to electrode 164 via tube 176, e.g., for electrogram sensing and/or pacing.

IMD 14 may include valve 178 coupled to port 174 on distal end 102 of IMD 14 for opening and closing port 174. Valve 178 may be any suitable valve, such as a micro-actuated value, for controlling the release of drugs out of IMD 14 from through port 174. When valve 178 is closed, valve 178 keeps port 174 closed, thereby preventing IMD 14 from releasing the drugs contained in reservoir 170 out of reservoir 170 through port 174. When valve 178 is open, port 174 is opened, thereby allowing IMD 14 to release one or more doses of the drugs contained in reservoir 170 through port 174 into the heart wall of heart 8 and/or the bloodstream of heart 8. Valve 178 may include or be coupled to a valve actuator for controlling the operations of valve 178. The valve actuator for valve 178 may be coupled or otherwise connected to the electronics in control electronics subassembly 152 so that the electronics housed in control electronics subassembly 152 may control the valve actuator and control the opening and closing of valve 178.

In some examples, instead of being coupled to port 174, valve 178 may be coupled to reservoir 170 to control the release of the drugs contained in reservoir 170. When valve 178 is closed, valve 178 prevents reservoir 170 from releasing the drugs contained in reservoir 170 out of reservoir 170. When valve 178 is open, valve 178 allows reservoir 170 to release one or more doses of the drugs contained in reservoir 170 from reservoir 170 and out of port 174 into the heart wall of heart 8 and/or the bloodstream of heart 8.

In some examples, reservoir 170 is coupled to or includes pump 171, such as a pneumatic pump, a microfluidic pump, and the like for pumping, expelling, or otherwise causing the drugs contained in reservoir 170 to move towards and out of port 174 into the heart wall of heart 8 and/or the bloodstream of heart 8. Pump 171 may be configured so that when pump 171 is activated, pump 171 may operate to cause a single dosage of the drugs in reservoir 170 to be expelled out of port 174.

Control electronics subassembly 152 may house electronics for controlling the release of drugs contained in reservoir 170 into the heart wall of heart 8 and/or the bloodstream of heart 8 by controlling the actuation of valve 178. As described above, the electronics housed in control electronics subassembly 152 may be coupled to otherwise connected to valve 178 and/or the valve actuator for valve 178 as well as pump 171. For example, to open valve 178, the electronics may send a signal to the valve actuator for valve 178 that causes the valve actuator to open valve 178. To close valve 178, the electronics may send a signal to the valve actuator for valve 178 that causes the valve actuator to close valve 178. Similarly, the electronics may send a signal to pump 171 to cause pump 171 to expel one or more doses of the drug in reservoir 170 out of port 174.

The electronics of IMD 14 may detect, based on the cardiac signals sensed via electrodes 162 and 164 or based on communications from cardiac monitor 22, the occurrence of an arrhythmia in heart 8 and may, in response to detecting the occurrence of the arrhythmia in heart 8, control valve 178 to release a therapeutically useful dose of drugs from reservoir 170 out of port 174 into the heart wall of heart 8 and/or the bloodstream of heart 8 to treat the arrhythmia. That is, in response to detecting the occurrence of the arrhythmia in heart 8, the electronics may send a signal to valve 178 and/or the valve actuator of valve 178 that causes valve 178 to open and may send a signal to pump 171 that causes pump 171 to expel one or more doses of the drug in reservoir 170 out of port 174, thereby releasing the drugs contained in the reservoir 170 out of port 174 into the heart wall of heart 8 and/or the bloodstream of heart 8 to treat the arrhythmia. Once the electronics determine that a therapeutically useful dose of the drug has been released out of IMD 14, the electronics may send a signal to valve 178 and/or the valve actuator of valve 178 that causes valve 178 to close, thereby ceasing release of the drugs contained in the reservoir 170 out of port 174 into the heart wall of heart 8 and/or the bloodstream of heart 8. In some examples, in response to detecting the occurrence of the arrhythmia in heart 8, the electronics may also send a signal to external device 20 to indicate that an arrhythmia has occurred in heart 8 and that IMD 14 has released a dose of the drugs from reservoir 170 into the heart wall of heart 8 and/or the bloodstream of heart 8.

For example, if reservoir 170 contains drugs for treating tachycardia, such as adenosine, the electronics of IMD 14 may detect, based on the cardiac signals sensed via electrodes 162 and 164, the occurrence of tachycardia in heart 8 and may, in response to detecting the occurrence of tachycardia in heart 8, control valve 178 to release a therapeutically useful dose of drugs, such as adenosine, from reservoir 170 out of port 174 into the heart wall of heart 8 and/or the bloodstream of heart 8 to treat the tachycardia.

In another example, if reservoir 170 contains drugs for treating bradycardia, the electronics of IMD 14 may detect, based on the cardiac signals sensed via electrodes 162 and 164, the occurrence of bradycardia in heart 8 and may, in response to detecting the occurrence of bradycardia in heart 8, control valve 178 to release a therapeutically useful dose of drugs from reservoir 170 out of port 174 into the heart wall of heart 8 and/or the bloodstream of heart 8 to treat the bradycardia.

In some examples, IMD 14 may include multiple reservoirs each containing the same or different drug for treating arrhythmias that occur in heart 8. As shown in FIG. 2B, IMD 14 includes reservoir 170A and reservoir 170B, similar to reservoir 170 shown in FIG. 2A, that each contain one or more therapeutically useful doses of drugs, such as drugs for treating arrhythmias.

Reservoir 170A may be coupled to port 174 via tube 176 for conveying drugs from reservoir 170A to and out of port 174. Reservoir 170A may also be coupled to valve 178A, similar to valve 178 shown in FIG. 2A, to control the release of the drugs contained in reservoir 170A. When valve 178A is closed, valve 178A prevents reservoir 170A from releasing the drugs contained in reservoir 170A out of reservoir 170A. When valve 178A is open, valve 178A allows reservoir 170A to release one or more doses of the drugs contained in reservoir 170A from reservoir 170A and out of port 174 into the heart wall of heart 8 and/or the bloodstream of heart 8. In some examples, reservoir 170A may include refill port 151A, similar to refill port 151 shown in FIG. 2A, for refilling reservoir 170A. Refill port 151A may extend from reservoir 170A through to an opening of housing 150, so that reservoir 170A may be refilled through refill port 151A.

Reservoir 170B may be coupled to port 174 via tube 176 for conveying drugs from reservoir 170B to and out of port 174. Reservoir 170B may also be coupled to valve 178B, similar to valve 178 shown in FIG. 2A, to control the release of the drugs contained in reservoir 170B. When valve 178B is closed, valve 178B prevents reservoir 170B from releasing the drugs contained in reservoir 170B out of reservoir 170B. When valve 178B is open, valve 178B allows reservoir 170B to release one or more doses of the drugs contained in reservoir 170B from reservoir 170B and out of port 174 into the heart wall of heart 8 and/or the bloodstream of heart 8. In some examples, reservoir 170B may include refill port 151B, similar to refill port 151 shown in FIG. 2A, for refilling reservoir 170B. Refill port 151B may extend from reservoir 170B through to an opening of housing 150, so that reservoir 170B may be refilled through refill port 151B.

Reservoir 170A is coupled to or includes pump 171A, similar to pump 171 shown in FIG. 2A, for pumping the drugs contained in reservoir 170A to move towards and out of port 174 into the heart wall of heart 8 and/or the bloodstream of heart 8. Pump 171A may be configured so that when pump 171A is activated, pump 171A may operate to cause a single dosage of the drugs in reservoir 170A to be expelled out of port 174.

Similarly, reservoir 170B is coupled to or includes pump 171B, similar to pump 171 shown in FIG. 2A, for pumping the drugs contained in reservoir 170A to move towards and out of port 174 into the heart wall of heart 8 and/or the bloodstream of heart 8. Pump 171B may be configured so that when pump 171B is activated, pump 171B may operate to cause a single dosage of the drugs in reservoir 170B to be expelled out of port 174.

The electronics housed in control electronics subassembly 152 may be coupled to otherwise connected to valves 178A and 178B and/or the valve actuator for valves 178A and 178B as well as pumps 171A and 171B. For example, to open valve 178A, the electronics may send a signal to the valve actuator for valve 178A that causes the valve actuator to open valve 178A. To close valve 178A, the electronics may send a signal to the valve actuator for valve 178A that causes the valve actuator to close valve 178A. Similarly, the electronics may send a signal to pump 171A to cause pump 171A to expel one or more doses of the drug in reservoir 170A out of port 174.

Correspondingly, to open valve 178B, the electronics may send a signal to the valve actuator for valve 178B that causes the valve actuator to open valve 178B. To close valve 178B, the electronics may send a signal to the valve actuator for valve 178B that causes the valve actuator to close valve 178B. Similarly, the electronics may send a signal to pump 171B to cause pump 171B to expel one or more doses of the drug in reservoir 170B out of port 174.

The electronics of IMD 14 may detect, based on the cardiac signals sensed via electrodes 162 and 164 or based on communications from cardiac monitor 22, the occurrence of an arrhythmia in heart 8 and may, in response to detecting the occurrence of the arrhythmia in heart 8, control valve 178 to release a therapeutically useful dose of drugs from reservoir 170A or reservoir 170B out of port 174 into the heart wall of heart 8 and/or the bloodstream of heart 8 to treat the arrhythmia. In some examples, reservoir 170A and reservoir 170B may contain different drugs, such as different drugs for treating different types of tachycardias. For example, reservoir 170A may contain drugs for treating ventricular tachycardia and reservoir 170B may contain drugs for treating supraventricular tachycardia. Thus, the electronics of IMD 14 may detect, based on the cardiac signals sensed via electrodes 162 and 164 or based on communications from cardiac monitor 22, not the occurrence of an arrhythmia in heart 8 but may also detect the type of arrhythmia that occurred in heart 8.

The electronics may, based on the type of arrhythmia that occurred in heart 8, determine whether to release drugs from reservoir 170A or to release drugs from reservoir 170B. The electronics may, in response to determining to release drugs from reservoir 170A to treat the detected type of arrhythmia, send a signal to valve 178A and/or the valve actuator of valve 178A that causes valve 178A to open and may send a signal to pump 171A that causes pump 171A to expel one or more doses of the drug in reservoir 170A out of port 174, thereby releasing the drugs contained in the reservoir 170A out of port 174 into the heart wall of heart 8 and/or the bloodstream of heart 8 to treat the arrhythmia. Once the electronics determine that a therapeutically useful dose of the drug has been released out of reservoir 170A IMD 14, the electronics may send a signal to valve 178A and/or the valve actuator of valve 178A that causes valve 178A to close, thereby ceasing release of the drugs contained in the reservoir 170A out of port 174A into the heart wall of heart 8 and/or the bloodstream of heart 8.

Similarly, the electronics may, based on the type of arrhythmia that occurred in heart 8, determine whether to release drugs from reservoir 170B or to release drugs from reservoir 170B. The electronics may, in response to determining to release drugs from reservoir 170B to treat the detected type of arrhythmia, send a signal to valve 178B and/or the valve actuator of valve 178B that causes valve 178B to open and may send a signal to pump 171B that causes pump 171B to expel one or more doses of the drug in reservoir 170B out of port 174, thereby releasing the drugs contained in the reservoir 170B out of port 174 into the heart wall of heart 8 and/or the bloodstream of heart 8 to treat the arrhythmia. Once the electronics determine that a therapeutically useful dose of the drug has been released out of reservoir 170B IMD 14, the electronics may send a signal to valve 178B and/or the valve actuator of valve 178B that causes valve 178B to close, thereby ceasing release of the drugs contained in the reservoir 170B out of port 174A into the heart wall of heart 8 and/or the bloodstream of heart 8.

Figure 3:
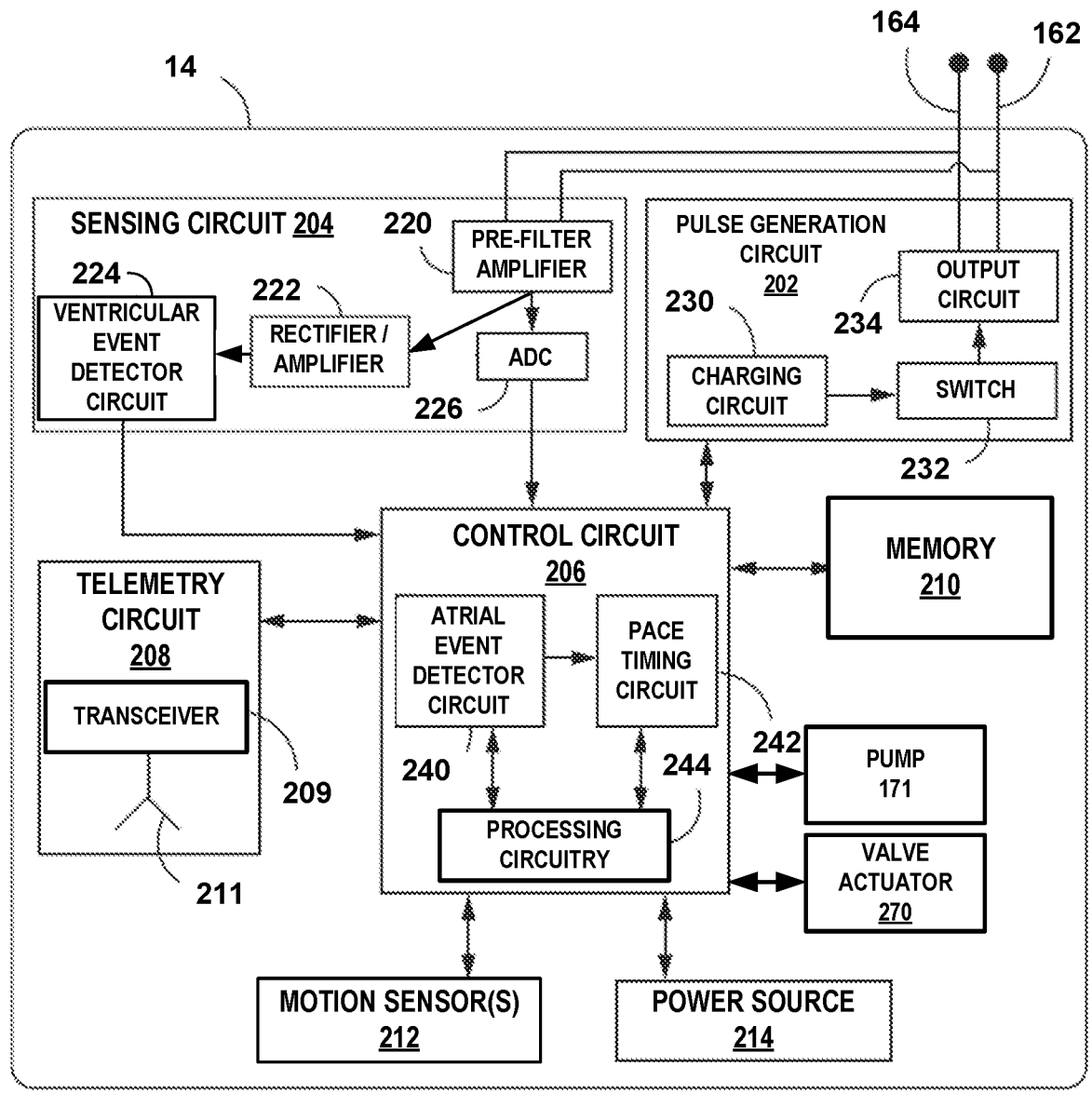
FIG. 3 is a block diagram illustrating an example configuration of the IMD of FIG. 1 in accordance with the techniques of the disclosure.

FIG. 3 is a block diagram of an example configuration of IMD 14 of FIG. 1 in accordance with the techniques of the disclosure. IMD 14 includes a sensing circuit 204, a control circuit 206, memory 210, telemetry circuit 208, motion sensor 212 and a power source 214. If IMD 14 is an intracardiac ventricular pacemaker, IMD 14 may also include pulse generation circuit 202.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 may be a multi-axis sensor, e.g., a two-dimensional or three-dimensional sensor, with each axis providing a signal that may be analyzed individually or in combination for detecting cardiac mechanical events. In the example of FIG. 3, motion sensor 212 is implemented as an accelerometer and may also be referred to herein as "accelerometer 212." However, in other examples, motion sensor 212 is another type of motion sensor or mechanical sensor capable of detecting mechanical motion of heart 8, such as a piezoelectric sensor or a MEMS device. Motion sensor 212 produces an electrical signal correlated to mechanical motion or vibration of sensor 212 (and IMD 14), e.g., when subjected to flowing blood and cardiac motion. The motion sensor 212 may include, e.g., filters, amplifiers, rectifiers, an ADC and/or other components for producing a mechanical motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 to Ruben, et al., entitled "Shock resistant accelerometer for implantable medical device," filed on Jul. 31, 1997 and issued on Mar. 23, 1999, the entire content of which is incorporated herein by reference. Additional detail with respect to an implantable medical device arrangement including a piezoelectric accelerometer for detecting patient motion is set forth in U.S. Pat. No. 4,485,813 to Anderson, et al., entitled "Implantable dynamic pressure transducer system," filed on Nov. 19, 1981, and issued on Dec. 4, 1984, and U.S. Pat. No. 5,052,388 to Sivula, et al., entitled "Method and apparatus for implementing activity sensing in a pulse generator," filed on Dec. 22, 1989, and issued on Oct. 1, 1991, the entire contents of each of which is incorporated by reference herein. Examples of three-dimensional accelerometers that may be implemented in IMD 14 and used for detecting cardiac mechanical events is set forth in in U.S. Pat. No. 5,593,431 to Sheldon, entitled "Medical service employing multiple DC accelerometers for patient activity and posture sensing and method," filed on Mar. 30, 1995 and issued on Jan. 14, 1997, and U.S. Pat. No. 6,044,297 to Sheldon, entitled "Posture and device orientation and calibration for implantable medical devices," filed on Sep. 25, 1998, and issued on Mar. 28, 2000, the entire contents of each of which are incorporated herein by reference. Other accelerometer designs may be used for producing an electrical signal that is correlated to motion imparted on IMD 14 due to ventricular and atrial events.

Sensing circuit 204 is configured to sense electrogram data by sensing a cardiac electrical signal via electrodes 162 and 164 by a pre-filter and amplifier circuit 220. Pre-filter and amplifier circuit 220 may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to rectifier/amplifier 222 and analog-to-digital converter (ADC) 226. ADC 226 may pass a multi-bit, digital electrogram (EGM) signal to control circuit 206 for use, in some cases, by atrial event detector circuit 240 for detecting atrial electrical events, such as P-waves. For example, atrial event detector circuit 240 may use identification of atrial electrical events in algorithms for detecting atrial systolic events from the mechanical motion signal provided by motion sensors 212. The amplified signal of pre-filter and amplifier circuit 220 may also be passed to rectifier and amplifier circuit 222, which may include a rectifier, bandpass filter, and amplifier for passing a cardiac signal to ventricular event detector circuit 224 for use in identifying ventricular electrical events (e.g., R-waves or T-waves).

Ventricular event detector circuit 224 may include a sense amplifier or other detection circuitry that compares the incoming rectified, cardiac electrical signal to a ventricular event detection threshold, which may be an auto-adjusting threshold. In some examples, ventricular event detector circuit 224 is configured to detect ventricular events, such as an R-wave or a T-wave. When the incoming signal crosses the ventricular event detection threshold, ventricular event detector circuit 224 produces a sensed ventricular event signal (e.g., which may be an R-sense signal where an R-wave is detected) that is passed to control circuit 206. In other examples not expressly depicted in the example of FIG. 3, ventricular event detector circuit 224 may be configured to receive a digital output of ADC 226 for detecting ventricular events by a comparator, morphological signal analysis of the digital EGM signal, or to perform other ventricular event detection techniques. Sensed ventricular event signals passed from ventricular event detector circuit 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 may include an atrial event detector circuit 240, pace timing circuit 242, and processing circuitry 244. While FIG. 3 may be an example of a ventricular IMD, in some examples where IMD 14 is an atrial IMD, atrial event detector circuit 240 may be included in sensing circuit 204. Atrial detector circuit 240 may be configured to detect atrial mechanical events from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

In some examples, atrial detector circuit 240 may be configured to detect atrial mechanical events based on signals received from sensing circuitry 204, such as sensed ventricular event signals (e.g., sensed R-wave events, digital electrogram data, and/or any other sensed ventricular event signals). In some examples, if IMD 14 is a ventricular IMD, control circuit 206 may also be configured to detect atrial events by receiving one or more signals from another IMD, such as an atrial IMD or an IMD implanted elsewhere in the patient, that is configured to detect electrical or mechanical atrial signals.

Control circuit 206 may receive sensed ventricular event signals, such as sensed R-wave events, and/or digital electrogram data from sensing circuit 204 for use in detecting and confirming cardiac events and optionally controlling ventricular pacing if IMD 14 performs the functionality of a cardiac pacemaker. For example, R-wave sensed event signals may be passed to pace timing circuit 242 for inhibiting scheduled ventricular pacing pulses or scheduling ventricular pacing pulses when IMD 14 is operating in a non-atrial tracking (asynchronous) ventricular pacing mode. R-wave sensed event signals may also be passed to atrial event detector circuit 240 for use in setting time windows used by control circuit 206 for detecting atrial systolic events from the motion sensor signal.

Atrial event detector circuit 240 receives a mechanical motion signal from motion sensor 212 and may start an atrial refractory period in response to a ventricular electrical event, e.g., an R-wave sensed event signal from sensing circuit 204 or delivery of a ventricular pacing pulse by pulse generation circuit 202. In some examples, atrial event detector circuit 240 determines if the motion sensor signal satisfies atrial mechanical event detection criteria outside of the refractory period. The motion sensor signal during the refractory period may be monitored by atrial event detector circuit 240 for the purposes of detecting ventricular mechanical events, which may be used for confirming or validating atrial systolic event detection.

Atrial event detector circuit 240 passes an atrial event detection signal to processing circuitry 244 and/or pace timing circuit 242 in response to detecting an atrial systolic event from the motion sensor signal. In other examples, the atrial systolic event may be detected as a mechanical event from the motion sensor signal. Additional description with respect to atrial systolic event sensing or detection for use in controlling atrial synchronized ventricular pacing by an intracardiac ventricular pacemaker are set forth in U.S. Patent Application Pub. No. 2018/0161580 to Demmer, et al., entitled "INPUT SWITCHING IN A VENTRICULAR INTRACARDIAC PACEMAKER," filed on Dec. 13, 2016, and published on Jun. 14, 2018, the entire contents of which are incorporated by reference herein.

Pace timing circuit 242 (or processing circuitry 244) may additionally receive sensed ventricular event signals, such as sensed R-wave event signals, from ventricular event detector circuit 224 for use in controlling the timing of pacing pulses delivered by pulse generation circuit 202. In some examples, processing circuitry 244 is one or more microprocessors, digital signal processors (DSPs), application specific integrated circuits (ASICs), field programmable gate arrays (FPGAs), or any other equivalent integrated or discrete logic circuitry, as well as any combinations of such components. Processing circuitry 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processing circuitry 244 for use in setting the AV pacing interval used by pace timing circuit 242.

Pace timing circuit 242 may additionally include a lower pacing rate interval timer for controlling a lower ventricular pacing rate. For example, if an atrial systolic event is not detected from the motion sensor signal, thus not initiating the programmed AV pacing interval for triggering a ventricular pacing pulse, a ventricular pacing pulse may nevertheless be delivered by pulse generation circuit 202 upon expiration of the lower pacing rate interval to prevent ventricular asystole and maintain a minimum ventricular rate.

Processing circuitry 244 may retrieve other programmable pacing control parameters, such as pacing pulse amplitude and pacing pulse width, which are passed to pulse generation circuit 202 for controlling pacing pulse delivery from memory 210. In addition to providing control signals to pace timing circuit 242 and pulse generation circuit 202 for controlling pacing pulse delivery, processing circuitry 244 may provide sensing control signals to sensing circuit 204, e.g., ventricular event sensing thresholds such as an R-wave sensing threshold, sensitivity, and/or various blanking and refractory intervals applied to the electrogram data.

Pulse generation circuit 202 generates electrical pacing pulses that are delivered to the RV of the patient's heart via cathode electrode 164 and return anode electrode 162. Pulse generation circuit 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval, a VV rate smoothing interval, or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Additional description of pacing circuitry is set forth in U.S. Pat. No. 5,507,782 to Kieval, et al., entitled "Method and apparatus for dual chamber cardiac pacing," filed on Mar. 17, 1994 and issued on Apr. 16, 1996 and U.S. Pat. No. 8,532,785 to Crutchfield, et al., entitled "Therapy delivery method and system for implantable medical devices," filed on Sep. 26, 2012, and issued on Sep. 10, 2013, the entire contents of each of which are incorporated herein by reference. Such pacing circuitry described by U.S. Pat. Nos. 5,507,782 and 8,532,785 may be implemented in IMD 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to IMD 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media.

Power source 214 provides power to each of the other circuits and components of IMD 14 as required. Power source 214 may include one or more energy storage devices, such as one or more rechargeable or non-rechargeable batteries. The connections between power source 214 and other circuits and components of IMD 14 are not shown in FIG. 3 for the sake of clarity but are to be understood from the general block diagram of FIG. 3. For example power source 214 may provide power to charging circuit 230 for charging a holding capacitor to a pacing voltage amplitude, current to switching circuit 232 and other circuitry included in pulse generation circuit 202 as needed, power to transceiver 209, motion sensor 212, and ADC 226 and other circuitry of sensing circuit 204 as needed as well as memory 210.

Telemetry circuit 208 includes a transceiver 209 and antenna 211 for transferring and receiving data via a radio frequency (RF) communication link. Telemetry circuit 208 may be capable of bi-directional communication with external device 20 and cardiac monitor 22 (FIG. 1) as described above. For example, IMD 14 may receive, via telemetry circuit 208 from cardiac monitor 22, an indication of an occurrence of an arrhythmia in heart 8, such as the occurrence of a tachycardia or the occurrence of a bradycardia, detected by cardiac monitor 22. In some examples, IMD 14 may receive, via telemetry circuit 208 from cardiac monitor 22, electrogram data sensed by cardiac monitor 22 that processing circuitry 244 may process to detect the occurrence of an arrhythmia in heart 8. In some instances, IMD 14 may rely solely on a communication from an external device, such as cardiac monitor 22, to identify the tachycardia or bradycardia or other cardia rhythm condition, thus possibly eliminating the need for sensing circuit 204 or pulse generation circuit 202.

Mechanical motion data and electrogram data may be transmitted by telemetry circuit 208 to external device 20. Furthermore, event detection parameters, pacing control parameters, and algorithms for performing atrial event detection and/or ventricular pacing control may be received by telemetry circuit 208 and stored in memory 210 for access by control circuit 206.

IMD 14 may include pump 171 for pumping drugs out of reservoir 170 to be released into the heart wall of heart 8 and/or the bloodstream of heart 8. When IMD 14 includes valve 178 that maybe open and closed to control the release of drugs into the heart wall of heart 8 and/or the bloodstream of heart 8, IMD 14 may include valve actuator 270 to control the actuation of valve 178. That is, valve actuator 270 may control the opening and closing of valve 178. IMD 14 may, in some examples, not include pump 171. In examples where IMD 14 does not include pump 171, IMD 14 may use valve actuator 270 to control the actuation of valve 178 to thereby control the flow rate of drugs out of reservoir 170.

In accordance with the techniques of the disclosure, processing circuitry 244 of control circuit 206 may detect, using any suitable technique and based at least in part on signals received by control circuit 206 from sensing circuit 204, event detector circuit 240, and/or telemetry circuit 208, the occurrence of an arrhythmia in heart 8 in which IMD 14 is implanted. Examples of arrhythmias that can be detected by control circuit 206 may include tachycardia, fibrillation, bradycardia, as well as any other arrhythmias. In some examples, if reservoir 170 of IMD 14 contains only drugs for treating tachycardia, such as adenosine, processing circuitry 244 may only be configured to detect the occurrence of tachycardia for the purposes of delivering adenosine to treat the tachycardia. In some examples, if reservoir 170 of IMD 14 contains only drugs for treating bradycardia, processing circuitry 244 may only be configured to detect the occurrence of bradycardia for the purposes of delivering drugs to treat the bradycardia.

Processing circuitry 244 may, in response to detecting the occurrence of an arrhythmia in heart 8 and/or in response to receiving, from cardiac monitor 22 via telemetry circuit 208, an indication of the occurrence of an arrhythmia in heart 8, control pump 171 and valve actuator 270 to release a therapeutically useful dosage (e.g., 6-26 mg) of the drug stored in reservoir 170 into the heart wall of heart 8 and/or the bloodstream of heart 8. To control pump 171 and valve actuator 270, processing circuitry 244 may send one or more signals via a communications bus to pump 171 and valve actuator 270 that causes pump 171 to pump the drug stored in reservoir 170 and that causes valve actuator 270 to open valve 178, thereby releasing the drug stored in reservoir 170 into the heart wall of heart 8 and/or the bloodstream of heart 8 to treat the detected arrhythmia. Once IMD 14 has released the therapeutically useful dosage of the drug, processing circuitry 244 may send a signal via a communications bus to valve actuator 270 that causes valve actuator 270 to close valve 178.

Processing circuitry 244 may determine that IMD 14 has released a therapeutically useful dosage of the drug based on the amount of time that has elapsed after opening valve 178. For example, processing circuitry 244 may determine, such as from information stored in memory 210, the amount of time it takes for a therapeutically useful dosage of the drug stored in reservoir 170 to flow out of IMD 14 into the heart wall of heart 8 and/or the bloodstream of heart 8. Thus, processing circuitry 244 may, in response to sending a signal to valve actuator 270 that causes valve actuator 270 to open valve 178, wait until the amount of time specified for a therapeutically useful dosage of the drug stored in reservoir 170 to flow out of IMD 14 has elapsed before sending a signal to valve actuator 270 that causes valve actuator 270 to close valve 178.

IMD 14 may, in response to releasing a useful dosage of the drug stored in reservoir 170 to flow out of IMD 14 into the heart wall of heart 8 and/or the bloodstream of heart 8 to treat the occurrence of an arrhythmia, communicate with external device 20 via telemetry circuit 208 to send an indication to external device 20 that IMD 14 has releasing a useful dosage of the drug. Such information sent to external device 20 may be used by clinicians to monitor the status of the patient and/or determine whether a standard defibrillator should be implanted in the patient for treating the occurrences of arrhythmias.

Figure 4:
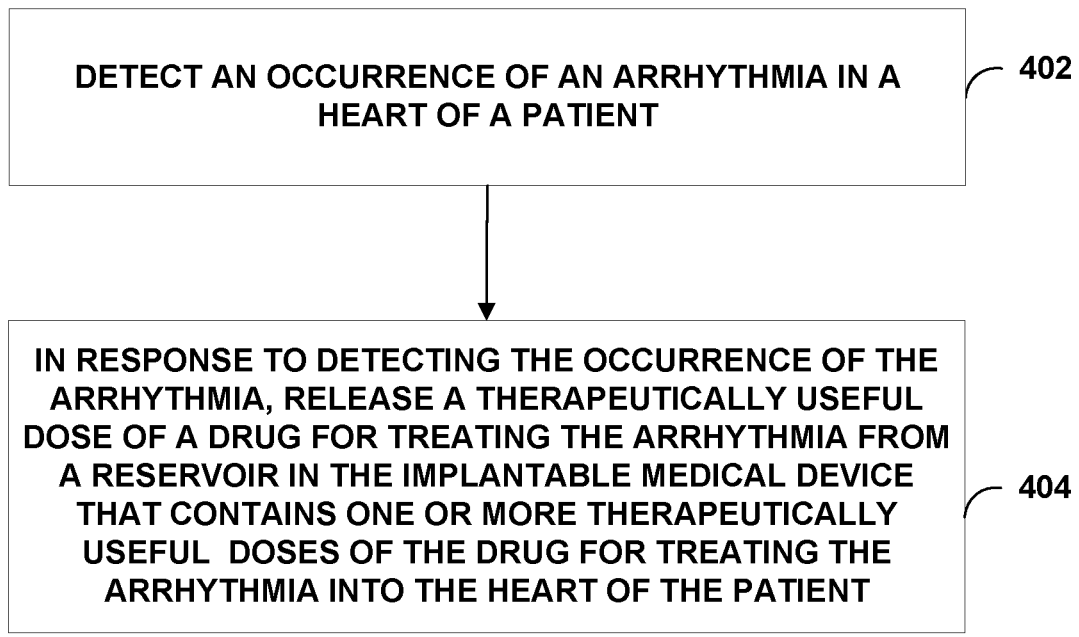
FIG. 4 is a flowchart illustrating an example operation for an implantable medical device to treat arrhythmias, in accordance with the techniques of the disclosure.

FIG. 4 is a flowchart illustrating an example operation for an implantable medical device to treat arrhythmias, in accordance with the techniques of the disclosure. Specifically, FIG. 4 illustrates an example operation for an IMD implanted in the heart of a patient to detect an arrhythmia and to release a therapeutically useful dose of a drug to treat the detected arrhythmia. For convenience, FIG. 4 is described with respect to FIGS. 1-3.

As shown in FIG. 4, processing circuitry 244 of IMD 14 may detect an occurrence of an arrhythmia in a heart 8 of a patient (402). In some examples, detecting the occurrence of the arrhythmia in the heart 8 of the patient may further include detecting an occurrence of tachycardia in the heart 8 of the patient. In some examples, the drug comprises adenosine. In some examples, detecting the occurrence of the arrhythmia in the heart 8 of the patient may further include detecting an occurrence of bradycardia in the heart 8 of the patient.

IMD 14 may, in response to detecting the occurrence of the arrhythmia, release a therapeutically useful dose of a drug for treating the arrhythmia from a reservoir 170 in the IMD 14 that contains one or more therapeutically useful doses of the drug for treating the arrhythmia into the heart 8 of the patient (404). In some examples, releasing the therapeutically useful dose of the drug for treating the arrhythmia from the reservoir 170 in the IMD 14 into the heart 8 of the patient further includes releasing therapeutically useful dose of the drug for treating the arrhythmia from the reservoir 170 in the IMD 14 out of a port 174 of the IMD 14 into the heart 8 of the patient, wherein the port 174 is disposed at a distal end 102 of the IMD 14, and wherein the distal end of the IMD 14 is a leading end as the IMD 14 is operable to contact a targeted site in the heart 8.

In some examples, releasing the therapeutically useful dose of the drug for treating the arrhythmia from the reservoir 170 in the IMD 14 into the heart 8 of the patient further includes opening a valve 178 in the IMD 14 to release the therapeutically useful dose of the drug out of a port 174 of the IMD 14 into the heart 8 of the patient. In some examples, IMD 14 may, in response to releasing the therapeutically useful dose of the drug out of the port 174 of the IMD 14 into the heart 8 of the patient, closing the valve 178 in the IMD 14 to prevent releasing additional doses of the drug.

In some examples, communication circuitry of IMD 14, such as telemetry circuit 208, may, in response to releasing the therapeutically useful dose of the drug into the heart 8 of the patient, output to an external device 20, via wireless communication, an indication that the IMD 14 has released the therapeutically useful dose of the drug into the heart 8 of the patient.

In some examples, the IMD 14 is adapted for implantation wholly within a heart chamber of the heart 8 of the patient, such as being adapted for implantation wholly within a right ventricle of the heart 8. In some examples, IMD 14 is an intracardiac pacemaker.

In some examples, IMD 14 further includes one or more electrodes 162 and 164 configured to sense electrogram data from the heart 8 of the patient, where the processing circuitry 244 of IMD 14 is configured to detect, based on the electrogram data, the occurrence of the arrhythmia in the heart 8 of the patient. In some example, to detect the occurrence of the arrhythmia in the heart 8 of the patient, the processing circuitry 244 of IMD 14 is further configured to receive, from a cardiac monitor via wireless communication, an indication of the occurrence of the arrhythmia in the heart 8 of the patient.

In some examples, in response to releasing the therapeutically useful dose of the drug, IMD 14 may continue to monitor for the occurrence of an arrhythmia in the heart 8 of the patient. IMD 14 may, in response to detecting the occurrence of an arrhythmia, release another therapeutically useful dose of the drug for treating the arrhythmia into the heart 8 of the patient or provide and/or provide stimulation therapy, such as anticardia pacing, via electrodes 162 and 164, to treat the detected arrhythmia.

In some examples, in response to releasing the therapeutically useful dose of the drug, IMD 14 may also monitor the effectiveness of the drugs in treating the detected medical condition. For example, IMD 14 may, in response to releasing the therapeutically useful dose of the drug for treating the detected arrhythmia, determine whether the arrhythmia is continuing to occur or whether the arrhythmia has stopped. IMD 14 may report such information, such as by outputting indications of the effectiveness of the drugs in treating the detected medical condition to external device 20, so that the patient or clinician may be able to determine whether the dosage of the drug released by IMD 14 was effective in treating the detected medical condition, and so that the clinician may be able to program IMD 14 via external device 20 to adjust the amount of the dosage of the drug released by IMD 14.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. An implantable medical device comprising:
   processing circuitry configured to detect an occurrence of an arrhythmia in a heart of a patient;
   a reservoir containing one or more therapeutically useful doses of a drug for treating the arrhythmia; and
   a valve operable to be opened in response to detection of the occurrence of the arrhythmia in the heart of the patient to release a therapeutically useful dose of the drug into the heart of the patient to treat arrhythmia of the heart;
   wherein the implantable medical device is adapted for one of implantation wholly within a heart chamber of the heart of the patient or within a pulmonary artery of the patient.

2. The implantable medical device of claim 1, wherein to detect the occurrence of the arrhythmia in the heart of the patient, the processing circuitry is further configured to:
   detect an occurrence of tachycardia in the heart of the patient.

3. The implantable medical device of claim 2, wherein the drug comprises adenosine.

4. The implantable medical device of claim 1, further comprising:
   a port for releasing the drug into the heart of the patient, wherein the port is disposed at an end of the implantable medical device, and wherein the end of the implantable medical device is operable to contact a targeted site in the heart.

5. The implantable medical device of claim 1, wherein the valve is operable to be closed after releasing the therapeutically useful dose of the drug into the heart of the patient.

6. The implantable medical device of claim 1, further comprising:
communication circuitry configured to, in response to releasing the therapeutically useful dose of the drug into the heart of the patient, output, to an external device, an indication that the implantable medical device has released the therapeutically useful dose of the drug into the heart of the patient.

7. The implantable medical device of claim 1, wherein the implantable medical device comprises an intracardiac pacemaker.

8. The implantable medical device of claim 1, wherein the implantable medical device is adapted for implantation wholly within a right ventricle of the heart.

9. The implantable device of claim 1, further comprising one or more electrodes configured to sense electrogram data from the heart of the patient, wherein the processing circuitry is configured to detect, based on the electrogram data, the occurrence of the arrhythmia in the heart of the patient.

10. The implantable device of claim 1, wherein to detect the occurrence of the arrhythmia in the heart of the patient, the processing circuitry is further configured to:
receive, from a cardiac monitor, an indication of the occurrence of the arrhythmia in the heart of the patient.

11. A method comprising:
detecting, by processing circuitry of an implantable medical device, an occurrence of an arrhythmia in a heart of a patient; and
in response to detecting the occurrence of the arrhythmia, releasing, by the implantable medical device, a therapeutically useful dose of a drug for treating the arrhythmia from a reservoir in the implantable medical device that contains one or more therapeutically useful doses of the drug for treating the arrhythmia into the heart of the patient;
wherein the implantable medical device is adapted for implantation wholly within a heart chamber of the heart of the patient.

12. The method of claim 11, wherein detecting the occurrence of the arrhythmia in the heart of the patient further comprises:
detecting, by the processing circuitry of the implantable medical device, an occurrence of tachycardia in the heart of the patient.

13. The method of claim 11, wherein the drug comprises adenosine.

14. The method of claim 11, wherein releasing the therapeutically useful dose of the drug for treating the arrhythmia from the reservoir in the implantable medical device into the heart of the patient further comprises:
releasing, by the implantable medical device, the therapeutically useful dose of the drug for treating the arrhythmia from the reservoir in the implantable medical device out of a port of the implantable medical device into the heart of the patient, wherein the port is disposed at an end of the implantable medical device, and wherein the end of the implantable medical device is operable to contact a targeted site in the heart.

15. The method of claim 11, wherein releasing the therapeutically useful dose of the drug for treating the arrhythmia from the reservoir in the implantable medical device into the heart of the patient further comprises:
opening, by the implantable medical device, a valve in the implantable medical device, to release the therapeutically useful dose of the drug out of a port of the implantable medical device into the heart of the patient.

16. The method of claim 11, further comprising:
in response to releasing the therapeutically useful dose of the drug into the heart of the patient, outputting, by the implantable medical device to an external device, an indication that the implantable medical device has released the therapeutically useful dose of the drug into the heart of the patient.

17. The method of claim 11, wherein the implantable medical device comprises an intracardiac pacemaker.

18. The method of claim 11, further comprising:
sensing, using one or more electrodes of the implantable medical device, electrogram data from the heart of the patient; and
detecting, by the processing circuitry and based on the electrogram data, the occurrence of the arrhythmia in the heart of the patient.

19. The method of claim 11, further comprising:
receiving, by the processing circuitry from a cardiac monitor, an indication of the occurrence of the arrhythmia in the heart of the patient.

20. An implantable medical device comprising:
one or more electrodes configured to sense electrogram data from a heart of a patient;
a reservoir containing one or more therapeutically useful doses of a drug for treating an arrhythmia;
a port for releasing the drug into the heart of the patient, wherein the port is disposed at a distal end of the implantable medical device;
a valve operable to be opened and closed; and
processing circuitry configured to:
detect, based on the electrogram data, an occurrence of the arrhythmia in the heart of the patient; and
in response to detecting the occurrence of the arrhythmia in the heart of the patient, cause the valve to be opened to release a therapeutically useful dose of the drug out of the port into the heart of the patient to treat arrhythmia of the heart;
wherein the implantable medical device is adapted for implantation wholly within a heart chamber of the heart of the patient.

* * * * *